United States Patent [19]
Capelle et al.

[11] Patent Number: 5,540,101
[45] Date of Patent: Jul. 30, 1996

[54] BOREHOLE DIRECTIONAL DILATOMETER

[75] Inventors: Jean-François Capelle, Montreal; Raoul Leroux; Etienne Dorig, both of Boucherville, all of Canada; Bernard Amadei, Boulder, Colo.

[73] Assignees: Roctest Ltd., St. Lambert, Canada; University of Colorado, Boulder, Colo.

[21] Appl. No.: 438,212

[22] Filed: May 9, 1995

[51] Int. Cl.$^6$ .................................................. G01N 3/00
[52] U.S. Cl. ................................................. 73/784; 73/783
[58] Field of Search ........................................ 73/784, 783

[56] References Cited

U.S. PATENT DOCUMENTS

| | | | |
|---|---|---|---|
| 4,030,345 | 6/1977 | Edmond et al. | 73/784 |
| 4,075,885 | 2/1978 | Handy et al. | 73/784 |
| 4,461,171 | 7/1984 | de la Cruz | 73/784 |
| 4,719,803 | 1/1988 | Capelle et al. | 73/784 |
| 4,733,568 | 3/1988 | Koopmans et al. | 73/784 |
| 4,760,741 | 8/1988 | Koopmans et al. | 73/784 |
| 4,962,668 | 10/1990 | Preston et al. | 73/784 |

FOREIGN PATENT DOCUMENTS 840203  4/1970  Canada.

OTHER PUBLICATIONS

Goodman, R. E. et al., Proc. 10th US Symp., on Rock Mechanics, pp. 523–555, 1972.
Heuze, F. E. et al., Int. J. Rock Mech. Min. Sci. + Geomech. Abstr., vol. 22, No. 2, pp. 105–112, 1985.
Amadei, B. et al., Proc. ISRM Symp. on Integral Approach to Applied Rock Mechanics, pp. 155–167, 1994.

Primary Examiner—Richard Chilcot
Assistant Examiner—Max Noori
Attorney, Agent, or Firm—Foley & Lardner

[57] ABSTRACT

A device positionable in a borehole for determining rock mass deformability, comprises a generally cylindrical body having at least one pair of diametrically opposed, elongated expandable wall portions for pressure contact engagement with the borehole wall, the wall portions being radially outwardly expandable in diametrically opposite directions along a predetermined axis extending transversely to the longitudinal axis of the borehole. An elongated core is arranged in the body and extends longitudinally thereof. A chamber is associated with a respective one of the expandable wall portions and is defined between the respective expandable wall portion and the core, the chambers associated with the at least one pair of expandable wall portions being in fluid communication for receiving a fluid under pressure. The device of the invention further includes an inlet for introducing the fluid under pressure into the associated chambers to cause the expandable wall portions to expand radially outwardly against the wall of the borehole, and a linear displacement sensor associated with a respective one of the expandable wall portions and mounted on the core, for measuring outward radial displacement of the respective expandable wall portion. The displacement sensor associated with the at least one pair of expandable wall portions are operative to provide signals indicative of borehole diametral deformation along the predetermined axis and thus of rock mass deformability.

23 Claims, 4 Drawing Sheets

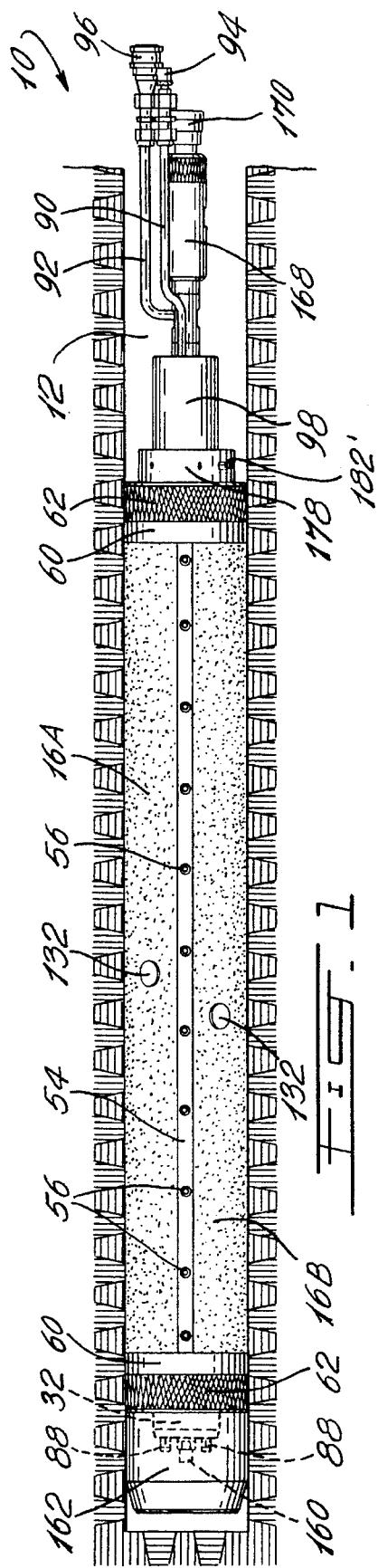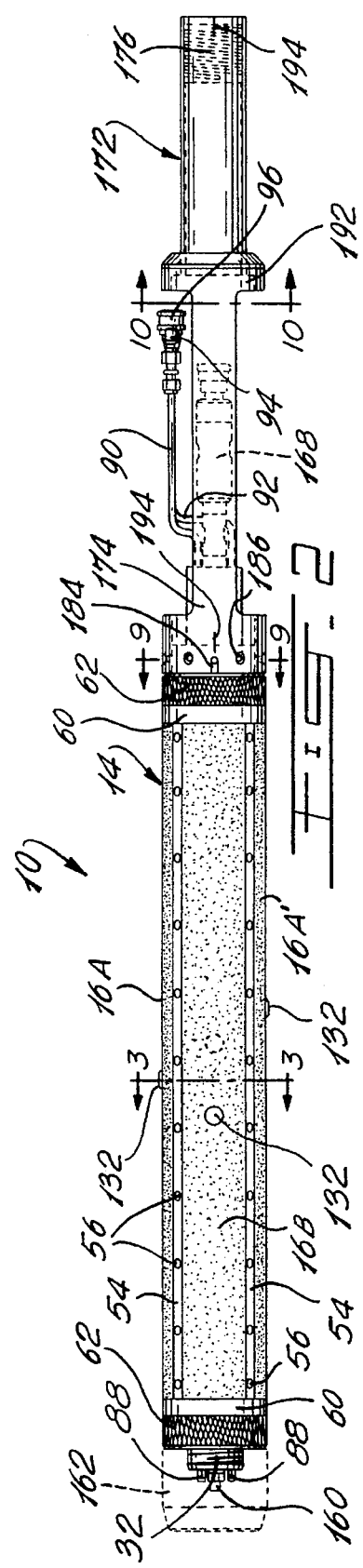

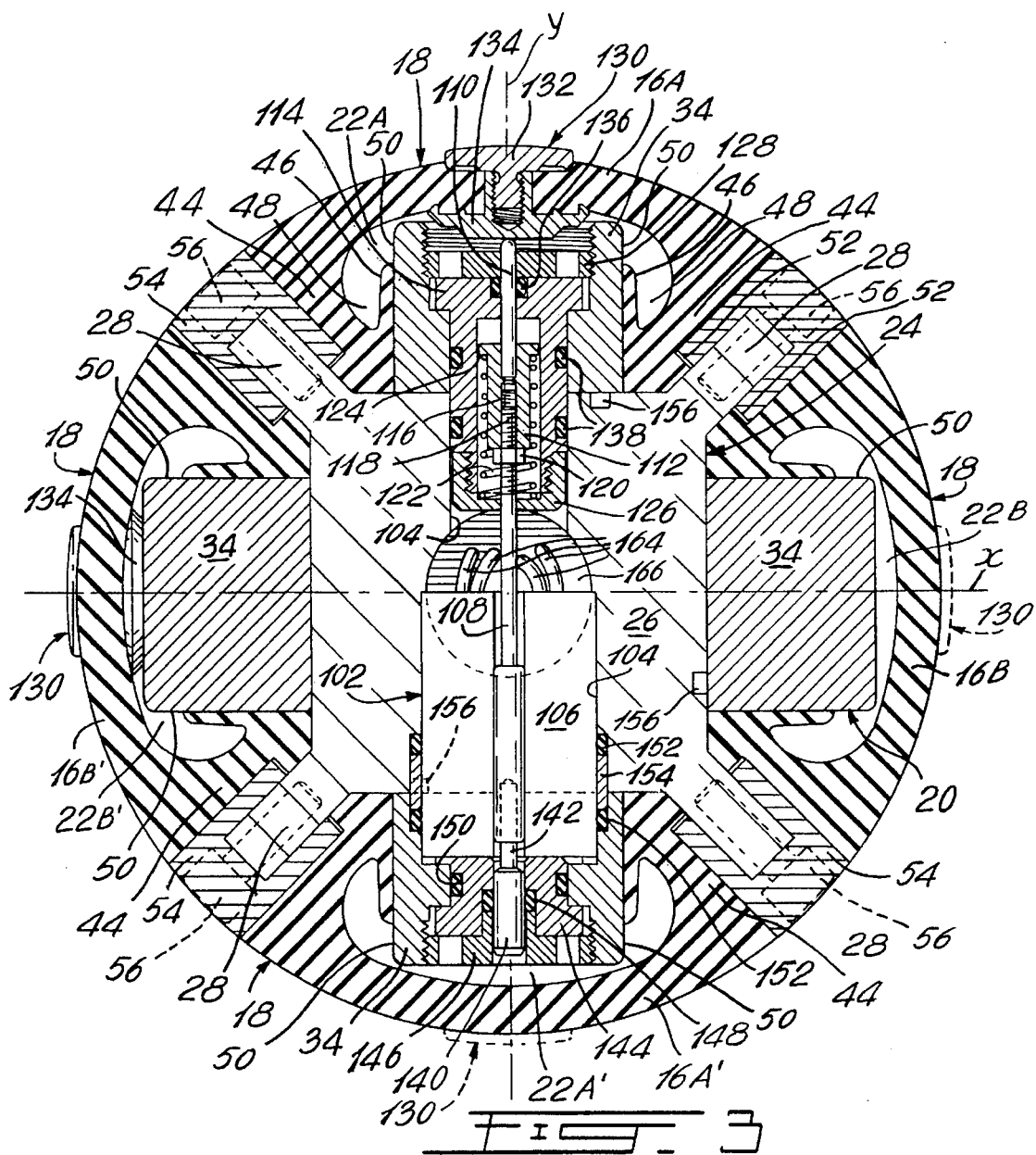

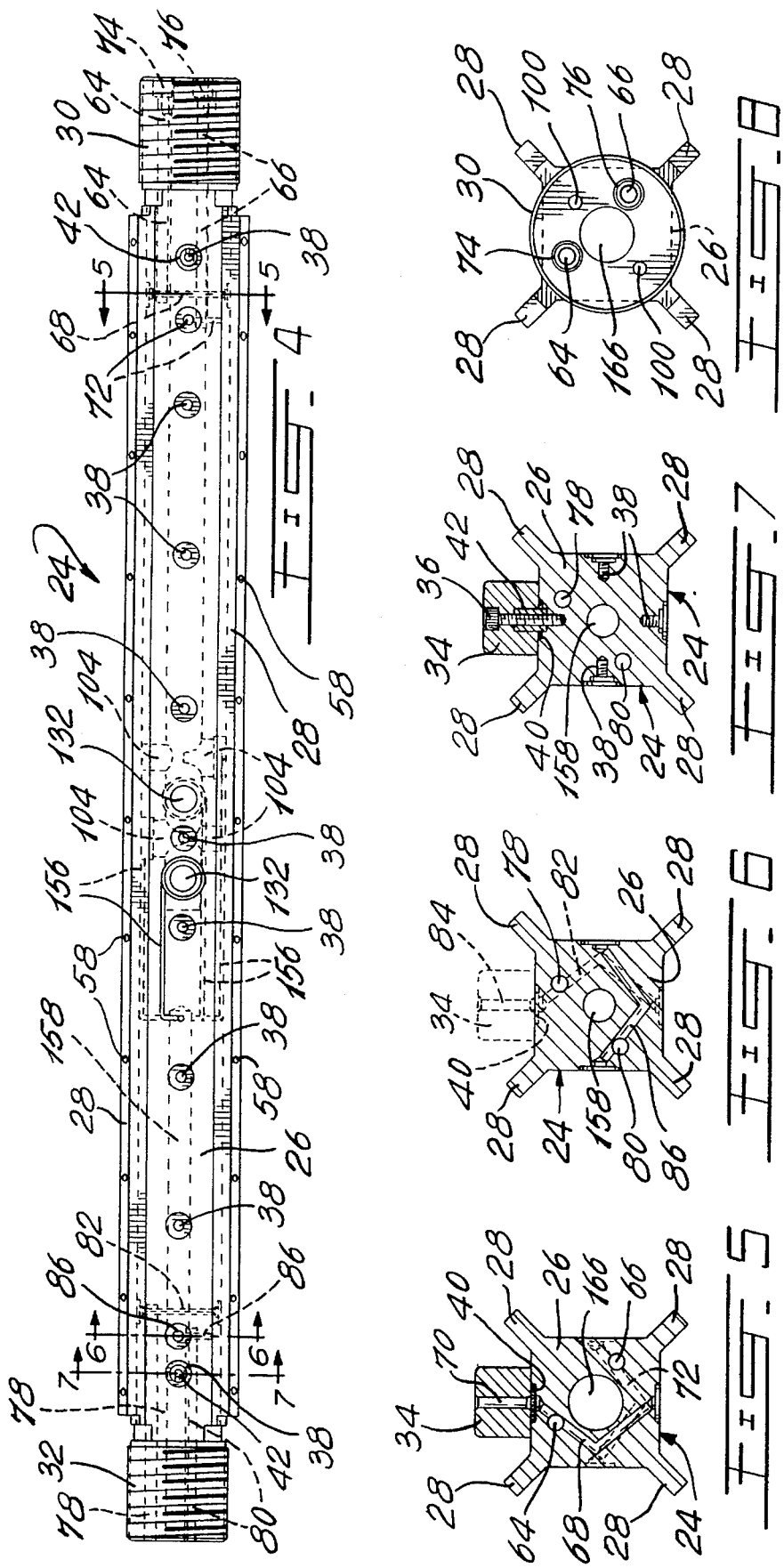

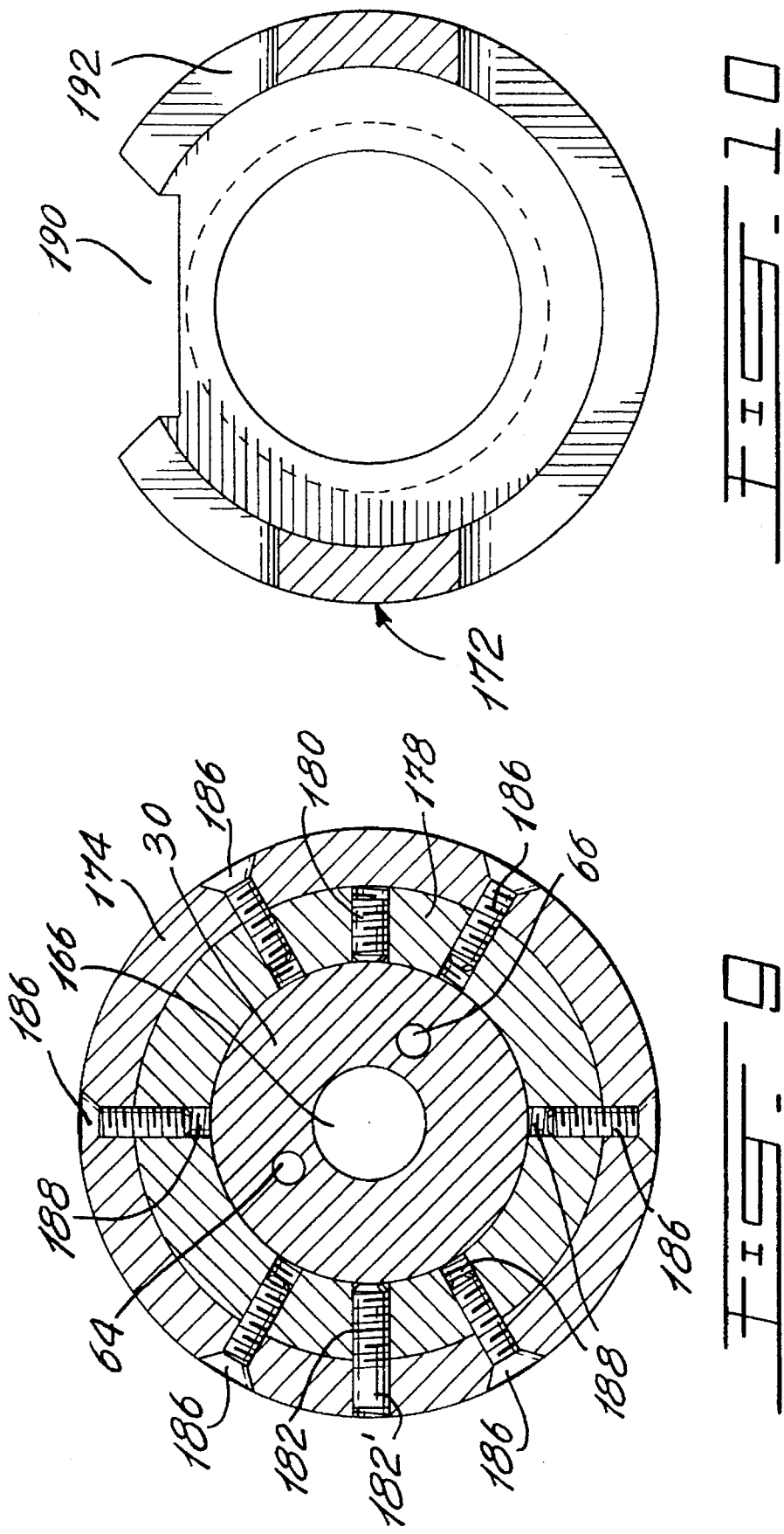

BOREHOLE DIRECTIONAL DILATOMETER

BACKGROUND OF THE INVENTION

The present invention relates to improvements in the field of borehole expansion testing. More particularly, the invention is concerned with an improved borehole dilatometer for determining the deformability of rock masses.

In general, laboratory tests on small rock specimens are inadequate to measure rock mass deformability because of scale effects. This limitation has led to the development of several static and dynamic field methods. In the static methods, loads are applied on selected rock surfaces in boreholes, underground galleries, or against surface exposures, and the resulting deformations are measured. These methods include plate bearing tests, flat jack tests, gallery tests and borehole expansion tests. Compared to large scale field tests, such as gallery and plate loading tests that are expensive and time consuming, borehole expansion tests can be conducted within a much more reasonable cost and time frame. However, they tend to involve smaller rock mass volumes.

A number of borehole testing devices are presently available which apply a load and measure the direct response of the borehole wall. These devices either (a) supply a uniform internal pressure to the borehole wall, such as dilatometers, or (b) supply a unidirectional pressure to a portion of the borehole wall by forcing apart two diametrically opposed curved steel platens, such as the NX-borehole jack described by Goodman, R. E. et al, in Proc. 10th US Symp. on Rock Mechanics, pp. 523–555, 1972, and by Heuze, F. E. et al, in Int. J. Rock Mech. Min. Sci., Vol. 22, No. 2, pp. 105–112, 1985. The results of these tests are often presented in the form of curves showing applied pressure versus diametral deformation. The diametral deformation is measured either in the direction of loading, as with the borehole jack, or at several locations around the borehole circumference as with the dilatometer described in Canadian Patent N°840,203.

Usually, borehole expansion test results are analyzed by modeling the rock mass as a linearly elastic, isotropic and homogeneous continuum with Young's modulus and Poisson's ratio. A value for the Poisson's ratio is assumed (often equal to 0.25) and the rock mass deformation modulus is determined from measured values of applied pressure and hole diametral deformation through equations borrowed from the theory of linear elasticity for isotropic media.

Existing dilatometers and the NX-borehole jack have several limitations. Dilatometers can only apply a uniform pressure along the wall of a borehole and are not directional, i.e., they cannot load the rock in a predetermined direction. Unless multiple transducers are installed in the instrument, any variations in diameter change around the borehole circumference due to inherent rock mass anisotropy, discontinuities and heterogeneities cannot be recorded. Many dilatometers still measure a volume change which is analyzed in terms of rock mass deformation by assuming that the rock is isotropic. On the other hand, the borehole jack was designed to apply directional loading in boreholes. However, the major flaw with the borehole jack is that the contact between the rock and the curved steel platens is not uniform and cannot be determined exactly, like for the dilatometers. The contact angle varies with the applied load and the difference in deformability between the steel and the rock. Since the contact angle enters into the calculation of the rock modulus of deformation, this may result in some errors when determining rock mass deformability.

SUMMARY OF THE INVENTION

It is therefore an object of the present invention to overcome the above drawbacks and to provide an improved borehole dilatometer which can apply a uniform pressure against the wall of a borehole in a predetermined transverse direction.

In accordance with the invention, there is provided a device positionable in a borehole for determining rock mass deformability, comprising a generally cylindrical body having at least one pair of diametrically opposed, elongated expandable wall portions for pressure contact engagement with the borehole wall, the wall portions being radially outwardly expandable in diametrically opposite directions along a predetermined axis extending transversely to the longitudinal axis of the borehole. An elongated core is arranged in the body and extends longitudinally thereof. A chamber is associated with a respective one of the expandable wall portions and is defined between the respective expandable wall portion and the core, the chambers associated with the at least one pair of expandable wall portions being in fluid communication for receiving a fluid under pressure. The device of the invention further includes inlet means for introducing the fluid under pressure into the associated chambers to cause the expandable wall portions to expand radially outwardly against the wall of the borehole, and a linear displacement sensing means associated with a respective one of the expandable wall portions and mounted on the core, for measuring outward radial displacement of the respective expandable wall portion. The displacement sensing means associated with the at least one pair of expandable wall portions are operative to provide signals indicative of borehole diametral deformation along the predetermined axis and thus of rock mass deformability.

The device according to the invention, hereinafter called directional dilatometer, enables one to effect the directional loading of the borehole wall with a radial pressure acting over two diametrically opposed expandable wall portions, with the expanded wall portions being always in perfect contact with the borehole wall.

In a preferred embodiment of the invention, each displacement sensing means includes an elongated radially movable sensor element normally biased in a direction toward the respective expandable wall portion for contact engagement therewith, whereby the outward radial displacement of the respective expandable wall portion is transmitted to the sensor element and is measured by the displacement sensing means. Such displacement sensing means preferably comprises a linear voltage displacement transducer having a slidable core rod coupled with the sensor element.

According to a particularly preferred embodiment, the expandable wall portions are each provided with a borehole wall contacting member formed of a non-compressible rigid material, the borehole contacting member extending through the expandable wall portion in fluid tight engagement therewith and being disposed in alignment with the sensor element for contact engagement therewith. The core rod and sensor element are advantageously coupled together by adjustable coupling means for adjustably moving the sensor element in direction toward or away from the borehole wall contacting member. Such adjustable coupling means preferably comprises a connector member fixed to one end of the sensor element and having a threaded bore in axial alignment with the sensor element, the threaded bore receiving a threaded end of the core rod to permit the connector member to be adjustably positioned along the threaded end, and a releasable lock member for releasably fixing the connector element to the threaded end of the core rod in a selected position.

Preferably, a spring means engages the connector member for normally biasing the connector member and the sensor element fixed thereto in a direction toward the borehole wall contacting member such that the other end of the sensor element is maintained in contact engagement with the borehole wall contacting member. A slidable piston is connected to the other end of the core rod opposite the threaded end. Each transducer extends through the core to permit fluid under pressure in the chamber associated with the expandable wall portion opposite the respective expandable wall portion to act upon the piston so as to urge the core rod and the sensor element coupled therewith in a direction toward the borehole wall contacting member and maintain the other end of the sensor element in contact engagement with the borehole wall contacting member upon increased pressure of the fluid in the associated chambers. The dilatometer of the invention further includes sealing means for preventing the fluid in the associated chambers from reaching each transducer.

According to another preferred embodiment, the expandable wall portions each comprise an elongated membrane mounted on the core in fluid tight engagement therewith. Each membrane comprises an inwardly extending peripheral flange having a terminal seal lip. The core comprises an elongated, longitudinally extending central core element and an elongated ridge member mounted on the core element and extending longitudinally thereof between opposed longitudinal portions and end portions of the peripheral flange, the ridge member having a peripheral seal abutment surface in sealing contact engagement with the seal lip. The longitudinal flange portions are each formed with an outer shoulder. The core element is provided with a rib extending along and adjacent each longitudinal flange portion. An elongated membrane retaining member engages the shoulder to releasably retain the longitudinal flange portion in abutting sealing engagement with the core element and the ridge member, the membrane retaining member being removably fixed to the rib by removable fastening means. Each chamber preferably includes a cavity defined between the peripheral flange and the seal lip, whereby the fluid under pressure in the cavity forces the seal lip against the seal abutment surface, and each longitudinal flange portion against the rib and the membrane retaining member, in sealing contact engagement therewith.

The directional dilatometer of the invention preferably comprises two pairs of membranes with the membranes of one pair being radially outwardly expandable in diametrically opposite directions along a first axis and the membranes of the other pair being radially outwardly expandable in diametrically opposite directions along a second axis, the first axis and second axis being orthogonal to one another. In such an embodiment, the core element comprises two pairs of ribs with the ribs of each pair extending outwardly along a diagonal axis and each rib extending between two adjacent membranes. Each membrane retaining member has a generally U-shaped cross-section for straddling each rib to releasably retain two adjacent membranes.

With the use of the directional dilatometer according to the invention, both the Young's modulus and Poisson's ratio of isotropic rock can be determined insitu. For an isotropic medium, the rock's Young's modulus, E, and Poisson's ratio, ν, can be determined concurrently by uniaxial loading of the walls of a single borehole. For each applied pressure increment, $\Delta p$, let $\Delta U_\parallel$=increment of diametral deformation measured in the loading direction, $\Delta U_\perp$=increment of diametral deformation measured at right angle to the loading direction, R=$\Delta U_\parallel / \Delta U_\perp$=ratio of diametral deformations.

The Poisson's ratio ν is equal to:

$$\nu = \frac{R(2A_{yx} + B_{yx}) - (A_{xx} + 2B_{xx})}{2[R(A_{yx} + B_{yx}) - (A_{xx} + B_{xx})]}$$

where:

$$A_{xx} = B_{yy} = -\frac{1}{\pi}\left[2\beta - \sin 2\beta + \sum_{m-2}^{N}\frac{1}{m}\left[-\frac{1}{m+1}(1 + (-1)^{m+1})\sin(m+1)\beta + \frac{1}{m-1}(1 + (-1)^{m-1})\sin(m-1)\beta\right]\right]$$

$$A_{yy} = B_{xx} = \frac{1}{\pi}\left[2\beta + \sin 2\beta + \sum_{m-2}^{N}\frac{1}{m}\left[\frac{1}{m+1}(1 + (-1)^{m+1})\sin(m+1)\beta + \frac{1}{m-1}(1 + (-1)^{m-1})\sin(m-1)\beta\right]\right]$$

$$A_{yx} = B_{xy} = \frac{1}{\pi}\left[2\beta - \sin 2\beta + \sum_{m-2}^{N}\frac{1}{m}\left[-\frac{1}{m+1}(1 + (-1)^{m+1})\sin(m+1)\beta + \frac{1}{m-1}(1 + (-1)^{m-1})\sin(m-1)\beta\right]\sin m\frac{\pi}{2}\right]$$

$$A_{xy} = B_{yx} = -\frac{1}{\pi}\left[2\beta + \sin 2\beta + \sum_{m-2}^{N}\frac{1}{m}\left[\frac{1}{m+1}(1 + (-1)^{m+1})\sin(m+1)\beta + \frac{1}{m-1}(1 + (-1)^{m-1})\sin(m-1)\beta\right]\sin m\frac{\pi}{2}\right]$$

β being the contact angle between the instrument and the rock.

The Young's modulus in the loading directions $E_\parallel$ is equal to:

$$E_\parallel = 2a\frac{\Delta p}{\Delta U_\parallel}(1+\nu)[(1-2\nu)A_{xx} + 2(1-\nu)B_{xx}]$$

The Young's modulus in the direction perpendicular to loading $E_\perp$ is equal to:

$$E_\perp = 2a\frac{\Delta p}{\Delta U_\perp}(1+\nu)[2(1-\nu)A_{yx} + (1-2\nu)B_{yx}]$$

Finally, the Young's modulus E=0.5 ($E_\parallel + E_\perp$),

BRIEF DESCRIPTION OF THE DRAWINGS

Further features and advantages of the invention will become more readily apparent from the following description of preferred embodiments as illustrated by way of example in the accompanying drawings, in which:

FIG. 1 is a side view of a directional dilatometer according to the invention, seen installed in a borehole;

FIG. 2 is a different side view of the directional dilatometer illustrated in FIG. 1, seen provided with an adapter member;

FIG. 3 is a sectional view taken along line 3—3 of FIG. 2;

FIG. 4 is a side view of the central core element of the dilatometer;

FIG. 5 is a sectional view taken along line 5—5 of FIG. 4, showing a ridge member mounted on the core element;

FIG. 6 is a sectional view taken along line 6—6 of FIG. 4;

FIG. 7 is a sectional view similar to FIG. 5 but taken along line 7—7 of FIG. 4;

FIG. 8 is a right end view of the central core element illustrated in FIG. 4;

FIG. 9 is a sectional view taken along line 9—9 of FIG. 2; and

FIG. 10 is a sectional view taken along line 10—10 of FIG. 2.

DESCRIPTION OF PREFERRED EMBODIMENTS

Referring first to FIGS. 1–3, there is illustrated a directional dilatometer generally designated by reference numeral 10. In FIG. 1, the dilatometer 10 is seen installed in a borehole 12. The dilatometer comprises a cylindrical body 14 having two pairs of diametrically opposed, elongated expandable wall portions h16A, 16A' and 16B,16B' with the wall portions 16A, 16A' being radially outwardly expandable in diametrically opposite directions along the y-axis and the wall portions 16B, 16B' being radially outwardly expandable in diametrically opposite directions along the x-axis. The expandable wall portions 16A, 16A', 16B, and 16B' each comprise an elongated membrane 18 mounted on an elongated core 20 arranged in the body 14 and extending longitudinally thereof. Four chambers 22A, 22A', 22B and 22B' are defined respectively between the expandable wall portions 16A, 16A', 16B,16B' and the core 20.

The core 20 comprises an elongated, longitudinally extending central core element 24 having a main body portion 26 of square cross-section with an outwardly extending rib 28 at each corner and two threaded cylindrical end portions 30 and 32 (shown in FIG. 4). The core 20 further comprises four elongated ridge members 34 mounted on the body portion 26, each ridge member 34 extending between two adjacent ribs 28. As shown in FIGS. 4 and 7, each ridge member 34 is releasably secured to the core element 24 by means of a plurality of screws 36 threadably engaged in threaded holes 38 formed in the body portion 26, a seal ring 40 being disposed in the orifice of each hole 38. Two tubular guide members 42 are arranged in the orifices of the holes 38 adjacent the end portions 30 and 32 for properly positioning the ridge members 34 on the body portion 26 during assembly.

As shown in FIG. 3, each membrane 18 comprises an inwardly extending peripheral flange 44 having a terminal seal lip 46, a cavity 48 being defined between the peripheral flange 44 and seal lip 46. The ridge members 34 each extend between opposed longitudinal portions and end portions (not shown) of the peripheral flange 44, each ridge member 34 having a peripheral seal abutment surface 50 in sealing contact engagement with the seal lip 46. The longitudinal flange portions are each formed with an outer shoulder 52, the end flange portions being formed with a similar shoulder (not shown). An elongated membrane retaining member 54 having a generally U-shaped cross-section straddles each rib 28 and releasably retains two adjacent membranes 18 by engaging the shoulders 52 thereof so as to retain two adjacent longitudinal flange portions in abutting sealing engagement with the body portion 26 of the core element 24 and adjacent ridge members 34. The membrane retaining members 54 are removably fixed to the ribs 28 by screws 56 threadably engaged in threaded holes 58 formed in each rib 28. Two membrane retaining rings 60 are provided for releasably retaining the end flange portions of each membrane 18 in abutting sealing engagement with each ridge member 34, the membrane retaining rings 60 being removably secured by knurled nuts 62 threadably engaging the threaded end portions 30,32 of the core element 24.

A fluid such as hydraulic oil is introduced under pressure into the chambers 22A, 22A' and/or 22B,22B' by means of two longitudinally extending inlet conduits 64 and 66 which are formed in the end portion 30 of the core element 24 and extend partially through the body portion 26, as shown in FIGS. 4, 5 and 8. The conduit 64 merges with a V-shaped conduit 68 extending in a transverse plane, the conduit 68 being in fluid communication with conduits 70 extending through opposite ridge members 34 (only one shown). Similarly, the conduit 66 merges with a V-shaped conduit 72 extending in a transverse plane, the conduit 72 being also in fluid communication with the conduits 70 of opposite ridge members 34 (not shown). Seal rings 40 (only one shown) are provided in the orifices of conduits 68 and 72. The orifices 74 and 76 of conduits 64 and 76 are also adapted to seatingly receive seal rings (not shown) and have chamfered edges to prevent the seal rings from being damaged during insertion. Thus, fluid under pressure is introduced into chambers 22A, 22A' via conduits 64,68,70 and/or into chambers 22B,22B' via conduits 66,72,70, the chambers 22A and 22A' being in fluid communication with one another by conduits 68,70 and the chambers 22B,22B' being in fluid communication with one another by conduits 72,70.

A similar arrangement is provided at the other end of the core element 24 for evacuating air from the chambers 22A, 22A', 22B and 22B' during the filling thereof with fluid. As shown, two longitudinally extending conduits 78 and 80 are formed in the end portion 32 of the core element 24, which extend partially through the body portion 26. The conduit 78 merges with a V-shaped conduit 82 extending in a transverse plane, the conduit 80 being in fluid communication with conduits 84 extending through opposite ridge members 34 (only one shown). Similarly, the conduit 80 merges with a V-shaped conduit 86 extending in a transverse plane, the conduit 86 being also in fluid communication with the conduits 84 of opposite ridge members 34 (not shown). Seal rings 40 (only one shown) are provided in the orifices of conduits 82 and 86. Thus, air initially contained in chambers 22A, 22A' and 22B,22B' is evacuated via conduits 78,82,84 and conduits 80,86,84, respectively, the chambers 22A and 22A' being in fluid communication with one another adjacent the end portion 32 by conduits 82,84 and the chambers 22B and 22B' being in fluid communication with one another by conduits 86,84. Once the air is evacuated from the chambers 22A, 22A', 22B and 22B' and the chambers are completely filled with fluid, the conduits 78 and 80 are closed with plugs 88, as shown in FIGS. 1 and 2.

Fluid is fed separately to the inlet conduits 64 and 66 by means of two metal tubes 90 and 92 provided with male and female quick connectors 94 and 96, respectively. The tubes 90,92 extend into a pressure transducer module 98 which is removably secured to the end portion 30 of the core element 24 by means of screws (not shown) threadably engaged in threaded holes 100 (shown in FIG. 8), the tubes 90 and 92 being in fluid communication with the conduits 64 and 66, respectively. The pressure transducer module 98 is operative to measure the pressure of the fluid in chambers 22A, 22A' and/or 22B,22B'.

Fluid introduced under pressure into the chambers 22A, 22A' and/or 22B,22B' causes the expandable wall portions 16A and 16A' to expand radially outwardly in diametrically opposite directions along the y-axis, and/or the expandable wall portions 16B and 16B' to expand radially outwardly in diametrically opposite directions along the x-axis. The dilatometer 10 includes four linear displacement sensing units 102 for separately measuring the outward radial displacement of the wall portions 22A, 22A',22B,22B', only one such unit 102 being shown in FIG. 3. As illustrated, the unit 102 extends through a bore 104 formed transversely in the core element 24 and comprises a linear voltage displacement transducer 106 having a slidable core rod 108 coupled with a sensor rod 110. The core rod 108 and sensor rod 110 are coupled together by means of a connector element 112 which is slidably movable in bushing 114. The connector element 112 is fixed to one end of the sensor rod 110 and has a threaded bore 116 in axial alignment with the sensor element, the threaded bore 116 receiving the threaded end 118 of the core rod 108 to permit the connector element 112 to adjustably positioned along the threaded end 118, so as to adjustably move the sensor element in a direction toward or away from the expandable wall portion 16A. A lock nut 120 is provided for releasably fixing the connector element to the threaded end of the core rod 108 in a selected position.

A coil spring 122 engages an annular shoulder 124 of the connector element 112 so as to normally bias the connector element 112 and the sensor rod 110 fixed thereto in a direction toward the wall portion 16A. The spring 122 is retained in a spring retainer cup 126 removably fixed to the bushing 114, the bushing being releasably secured by lock nut 128. The sensor rod 110 extends through the bushing 114 and lock nut 128 and is normally biased by spring 122 for contact engagement with a metallic contact button 130 which extends through the membrane 18 in fluid tight engagement therewith. The contact button 130 comprises a borehole wall contacting element 132 and a sensor contacting element 134 which are releasably secured to one another. Fluid thighness is ensured by means of seal rings 136 and 138. A slidable piston 140 is fixedly connected to the other end of the core rod 108 by means of a small shaft 142 which is press-fitted into the core rod. The piston 140 extends through a bushing 144 and lock nut 146. Fluid thighness is ensured by means of seal rings 148, 150 and 152, a tubular spacer member being disposed between the seal rings 152.

A groove 156 is formed in each sidewall of the core element 24 to define a conduit which is in fluid communication with a central, longitudinally extending conduit 158 (shown in FIG. 4), for evacuating any fluid which may accidentally leak adjacent each transducer 106. A check-valve 160 is provided in the outlet orifice of conduit 158. As shown in FIGS. 1 and 2, a protective head 160 threadably engages the end portion 32 of the core element 24 for protecting the plugs 88 and check-valve 160 during insertion of the dilatometer 10 in the borehole 12.

When fluid is introduced under pressure in the chambers 22A, 22A' and/or 22B,22B', the fluid under pressure in each cavity 48 forces the seal lip 46 against the seal abutment surface 50 of each ridge member 34, in sealing contact engagement therewith. The fluid under pressure in cavity 48 also forces the longitudinal portion of flange 44 against the rib 28 and the membrane retaining member 54. In addition, as shown in FIG. 3, fluid under pressure in the chamber 22A' acts on the piston 140 so as to urge the core rod 108 and the sensor rod 110 coupled therewith in a direction toward the contact button 130 and maintain the lead end of the sensor rod 110 in contact engagement with the sensor contacting element 134, upon increased pressure of the fluid in the chambers 22A, 22A'. The same action of the fluid on the piston 140 occurs in the chambers 22A, 22B and 22B'.

The outward radial displacements of the expandable wall portions 16A, 16A' and/or 16B,16B' are transmitted to the sensor rods 110 and core rods 108 and are measured by the transducers 106. The electrical signals of the transducers 106 are transmitted over wires 164 extending through a central bore 166 formed in the core element 24. The wires 164 extend through the pressure transducer module 98 and into a watertight housing 168 where they are connected along with the electrical wires (not shown) from the pressure transducer module, to a watertight electrical bus connector 170 for connection to a remote readout unit (not shown).

As shown in FIG. 2, a hollow cylindrical adapter member 172 extends rearwardly of the dilatometer 10 in axial alignment therewith. The adapter member 172 has one end portion 174 releasably connected to the end portion 30 of the core element 24, and an opposite internally threaded end portion 176 for engagement with a tubular extension (not shown) permitting the dilatometer 10 to be positioned at a predetermined depth in the borehole 12. The end portion 174 is connected to the end portion 30 by means of a threaded connector sleeve 178 which threadably engages the threaded end portion 30, the connector sleeve 178 being releasably secured to the latter by two set-screws 180 and 182 as shown in FIG. 9. The screw 182 is longer than the screw 180 and has a non-threaded portion 182' which protrudes from the connector sleeve 178 and serves as a guide pin. The end portion 174 of the adapter member 172 is provided with a guide slot 184 for receiving the guide pin 182' so as facilitate proper positioning of the adapter member 172. The end portion 174 is releasably secured to the connector sleeve 178 by screws 186 threadably engaged in threaded holes 188 formed in the connector sleeve.

The adapter member 172 has two diametrically opposed cut-out portions for exposing the metal tubes 90,92 and housing 168 and providing access to the male and female quick connectors 94,96 and electrical bus connector 170. As shown in FIG. 10, a notch 190 is defined in the flange 192 to enable the passage of fluid conduits and electrical cable (not shown) for connection to the connectors 94, 96 and 170. Two grooves 194 axially aligned with one another and with one of the borehole wall contact buttons 132 are formed in the adapter member 172 and provide visual marks permitting the expandable wall portions 16A, 16A' and/or 16B, 16B' to be oriented in the borehole 12 for radial outward expansion along a desired axis.

As it is apparent, the dilatometer 10 enables one to effect uniaxial or biaxial loading of the borehole wall 12.

We claim:

1. A device positionable in a borehole for determining rock mass deformability, comprising:

a generally cylindrical body having an elongated core extending longitudinally thereof and two pairs of diametrically opposed, elongated expandable wall portions for pressure contact engagement with the borehole wall, said expandable wall portions each comprising an elongated membrane mounted on said core in fluid tight engagement therewith, the membranes of one pair being radially outwardly expandable in diametrically opposite directions along a first axis and the membranes of the other pair being radially outwardly expandable in diametrically opposite directions along a second axis, said first axis and said second axis being orthogonal to one another;

a chamber associated with a respective one of said membranes and defined between each membrane and said core, the chambers associated with each pair of membranes being in fluid communication for receiving a fluid under pressure;

inlet means for introducing said fluid under pressure into the chambers associated with at least one selected pair of membranes to cause the membranes of said at least one selected pair to expand radially outwardly against the wall of said borehole; and a linear displacement sensing means associated with a respective one of said membranes and mounted on said core, for measuring outward radial displacement of said respective membrane, the displacement sensing means associated with each pair of membranes being operative to provide signals indicative of borehole diametral deformation along one of said first and second axes and thus of rock mass deformability.

2. A device positionable in a borehole for determining rock mass deformability, comprising:

a generally cylindrical body having at least one pair of diametrically opposed, elongated expandable wall portions for pressure contact engagement with the borehole wall, said wall portions being radially outwardly expandable in diametrically opposite directions along a predetermined axis extending transversely to a longitudinal axis of said borehole;

an elongated core arrangged in said body and extending longitudinally thereof;

a chamber associated with a respective one of said expandable wall portions and defined between said respective expandable wall portion and said core, the chambers associated with said at least one pair of expandable wall portions being in fluid communication for receiving a fluid under pressure;

inlet means for introducing said fluid under pressure into said associated chambers to cause said expandable wall portions to expand radially outwardly against the wall of said borehole; and a linear displacement sensing means associated with a respective one of said expandable wall portions and mounted on said core, for measuring outward radial displacement of said respective expandable wall portion, the displacement sensing means associated with said at least one pair of expandable wall portions being operative to provide signals indicative of borehole diametral deformation along said predetermined axis and thus of rock mass deformability;

wherein said expandable wall portions each comprise an elongated membrane mounted on said core in fluid tight engagement therewith;

wherein each membrane comprises an inwardly extending peripheral flange having a terminal seal lip, and wherein said core comprises an elongated, longitudinally extending central core element and an elongated ridge member mounted on said core element and extending longitudinally thereof between opposed longitudinal portions and end portions of said peripheral flange, said ridge member having a peripheral seal abutment surface in sealing contact engagement with said seal lip; and wherein said longitudinal flange portions are each formed with an outer shoulder and said core element is provided with a rib extending along and adjacent each longitudinal flange portion, and wherein an elongated membrane retaining member engages said shoulder to releasably retain said longitudinal flange portion in abutting sealing engagement with said core element and said ridge member, said membrane retaining member being removably fixed to said rib by removable fastening means.

3. A device as claimed in claim 1, wherein each membrane comprises an inwardly extending peripheral flange having a terminal seal lip, and wherein said core comprises an elongated, longitudinally extending central core element and an elongated ridge member mounted on said core element and extending longitudinally thereof between opposed longitudinal portions and end portions of said peripheral flange, said ridge member having a peripheral seal abutment surface in sealing contact engagement with said seal lip.

4. A device as claimed in claim 3, wherein each chamber includes a cavity defined between said peripheral flange and said seal lip, whereby said fluid under pressure in said cavity forces said seal lip against said seal abutment surface in sealing contact engagement therewith.

5. A device as claimed in claim 2, wherein each chamber includes a cavity defined between said peripheral flange and said seal lip, whereby said fluid under pressure in said cavity forces said seal lip against said seal abutment surface, and each said longitudinal flange portion against said rib and said membrane retaining member, in sealing contact engagement therewith.

6. A device as claimed in claim 1, wherein each displacement sensing means includes an elongated radially movable sensor element normally biased in a direction toward said respective membrane for contact engagement therewith, whereby the outward radial displacement of said respective membrane is transmitted to said sensor element and is measured by said displacement sensing means.

7. A device as claimed in claim 6, wherein each displacement sensing means comprises a linear voltage displacement transducer having a slidable core rod coupled with said sensor element.

8. A device as claimed in claim 7, wherein said membranes are each provided with a borehole wall contacting member formed of a non-compressible rigid material, said borehole contacting member extending through said membrane in fluid tight engagement therewith and being disposed in alignment with said sensor element for contact engagement therewith.

9. A device as claimed in claim 8, wherein said core rod and said sensor element are coupled together by adjustable coupling means for adjustably moving said sensor element in direction toward or away from said borehole wall contacting member.

10. A device as claimed in claim 9, wherein said adjustable coupling means comprises a connector member fixed to one end of said sensor element and having a threaded bore in axial alignment with said sensor element, said threaded bore receiving a threaded end of said core rod to permit said connector member to be adjustably positioned along said threaded end, and a releasable lock member for releasably fixing said connector element to said threaded end in a selected position.

11. A device as claimed in claim 10, wherein a spring means engages said connector member for normally biasing said connector member and said sensor element fixed thereto in a direction toward said borehole wall contacting member such that the other end of said sensor element is maintained in contact engagement with said borehole wall contacting member.

12. A device as claimed in claim 11, wherein a slidable piston is connected to the other end of said core rod opposite said threaded end and wherein each transducer extends through said core to permit fluid under pressure in the chamber associated with the membrane opposite said respective membrane to act upon said piston so as to urge said core rod and said sensor element coupled therewith in a direction toward said borehole wall contacting member and maintain said other end of said sensor element in contact engagement with said borehole wall contacting member upon increased pressure of said fluid in said associated chambers, said device further including sealing means for preventing said fluid in said associated chambers from reaching said transducer.

13. A device as claimed in claim 12, further including conduit means defined in said core for evacuating any fluid leaking adjacent each transducer.

14. A device as claimed in claim 2, wherein said body has two pairs of said membranes with the membranes of one pair being radially outwardly expandable in diametrically opposite directions along a first axis and the membranes of the other pair being radially outwardly expandable in diametrically opposite directions along a second axis, said first axis and said second axis being orthogonal to one another.

15. A device as claimed in claim 14, wherein said core element comprises two pairs of said ribs with the ribs of each pair extending outwardly along a diagonal axis and each rib extending between two adjacent membranes.

16. A device as claimed in claim 15, wherein each membrane retaining member has a generally U-shaped cross-section for straddling each said rib to releasably retain said two adjacent membranes.

17. A device as claimed in claim 1, wherein said body has a front end and a rear end, and wherein an elongated adapter member extends rearwardly of said body in axial alignment therewith and has one end releasably connected to said rear end and another end adapted for coupling engagement with extension means permitting said device to be positioned at a predetermined depth in said borehole.

18. A device as claimed in claim 17, wherein said adapter member is provided with visual marking means permitting the membranes of said at least one selected pair to be oriented in said borehole for radial outward expansion in diametrically opposite directions along at least one of said first and second axes.

19. A device as claimed in claim 1, further including pressure transducer means for measuring the pressure of said fluid in said associated chambers and for providing an electrical signal indicative of the measured pressure.

20. A device as claimed in claim 3, wherein said longitudinal flange portions are each formed with an outer shoulder and said core element is provided with a rib extending along and adjacent each longitudinal flange portion, and wherein an elongated membrane retaining member engages said shoulder to releasably retain said longitudinal flange portion in abutting sealing with said core element and said ridge member, said membrane retaining member being removably fixed to said rib by removable fastening means.

21. A device as claimed in claim 20, wherein each chamber includes a cavity defined between said peripheral flange and said seal lip, whereby said fluid under pressure in said cavity forces said seal lip against said seal abutment surface, and each said longitudinal flange portion against said rib and said membrane retaining member, in sealing contact engagement therewith.

22. A device as claimed in claim 20, wherein said core element comprises two pairs of said ribs with the ribs of each pair extending outwardly along a diagonal axis and each rib extending between two adjacent membranes.

23. A device as claimed in claim 22, wherein each membrane retaining member has a generally U-shaped cross-section for straddling each said rib to releasably retain said two adjacent membranes.

* * * * *